(12) United States Patent
Gibbs

(10) Patent No.: US 7,179,259 B1
(45) Date of Patent: Feb. 20, 2007

(54) INSTRUMENT ASSEMBLY FOR LATERAL IMPLANT

(75) Inventor: Philip M Gibbs, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 74 days.

(21) Appl. No.: 10/862,171

(22) Filed: Jun. 4, 2004

(51) Int. Cl.
*A61B 17/76* (2006.01)
*A61F 2/36* (2006.01)

(52) U.S. Cl. .......................... 606/64; 606/75; 606/98; 623/22.12

(58) Field of Classification Search .............. 606/62, 606/64, 96–99, 104; 623/22.12
See application file for complete search history.

(56) References Cited

U.S. PATENT DOCUMENTS

| | | | |
|---|---|---|---|
| 3,671,978 A | 6/1972 | May | |
| 3,815,590 A | 6/1974 | Deyerle | |
| 4,153,953 A * | 5/1979 | Grobbelaar | 623/23.27 |
| 4,306,550 A | 12/1981 | Forte | |
| D272,648 S | 2/1984 | Bolesky et al. | |
| D273,806 S | 5/1984 | Bolesky et al. | |
| 4,552,136 A | 11/1985 | Kenna | |
| 4,578,081 A | 3/1986 | Harder et al. | |
| D284,100 S | 6/1986 | Kenna | |
| 4,601,289 A | 7/1986 | Chiarizzio et al. | |
| 4,605,416 A * | 8/1986 | Grobbelaar | 623/23.27 |
| 4,667,664 A * | 5/1987 | Taylor et al. | 606/64 |
| 4,710,075 A * | 12/1987 | Davison | 408/202 |
| 4,790,854 A | 12/1988 | Harder et al. | |
| 4,822,370 A | 4/1989 | Schelhas | |
| 4,865,609 A | 9/1989 | Roche | |
| 4,921,493 A | 5/1990 | Webb, Jr. et al. | |
| 4,923,472 A | 5/1990 | Ugolini | |
| 4,963,155 A | 10/1990 | Lazzeri et al. | |
| 5,002,581 A | 3/1991 | Paxson et al. | |
| 5,019,108 A | 5/1991 | Bertin et al. | |
| 5,041,118 A | 8/1991 | Wasilewski | |
| 5,080,685 A | 1/1992 | Bolesky et al. | |
| 5,089,004 A | 2/1992 | Averill et al. | |
| 5,108,451 A | 4/1992 | Forte | |
| 5,116,379 A | 5/1992 | McLardy-Smith | |
| 5,156,627 A | 10/1992 | Amstutz et al. | |
| 5,181,928 A | 1/1993 | Bolesky et al. | |
| 5,201,769 A | 4/1993 | Schutzer | |
| 5,286,260 A | 2/1994 | Bolesky et al. | |
| 5,314,479 A | 5/1994 | Rockwood, Jr. et al. | |
| 5,342,366 A | 8/1994 | Whiteside et al. | |
| 5,358,526 A | 10/1994 | Tornier | |

(Continued)

OTHER PUBLICATIONS

"Alliance® Hip Systems," brochure, Biomet, Inc. (17 sheets).

(Continued)

*Primary Examiner*—Eduardo C. Robert
*Assistant Examiner*—Richard Shaffer
(74) *Attorney, Agent, or Firm*—Harness, Dickey & Pierce, P.L.C.

(57) ABSTRACT

An instrument assembly for inserting a lateral fastener into a lateral bore of a stem body implanted into a bone. The instrument assembly includes an outrigger having an alignment tube extending laterally from the stem body, wherein the outrigger can be coupled with the stem body such that the alignment tube extends coaxially with the lateral bore.

16 Claims, 10 Drawing Sheets

U.S. PATENT DOCUMENTS

| | | | |
|---|---|---|---|
| 5,370,706 A | 12/1994 | Bolesky et al. |
| 5,403,320 A | 4/1995 | Luman et al. |
| 5,458,654 A | 10/1995 | Tepic |
| 5,507,818 A | 4/1996 | McLaughlin |
| 5,507,830 A | 4/1996 | DeMane et al. |
| 5,549,706 A | 8/1996 | McCarthy |
| 5,601,567 A | 2/1997 | Swajger et al. |
| 5,607,431 A | 3/1997 | Dudasik et al. |
| 5,653,765 A | 8/1997 | McTighe et al. |
| 5,658,352 A | 8/1997 | Draenert |
| 5,704,940 A | 1/1998 | Garosi |
| 5,728,161 A | 3/1998 | Camino et al. |
| 5,766,261 A | 6/1998 | Neal et al. |
| 5,800,560 A | 9/1998 | Draenert |
| 5,860,969 A | 1/1999 | White et al. |
| 5,860,982 A | 1/1999 | Ro et al. |
| 5,885,295 A | 3/1999 | McDaniel et al. |
| 5,888,208 A | 3/1999 | Ro |
| 5,906,644 A | 5/1999 | Powell |
| 5,908,423 A | 6/1999 | Kashuba et al. |
| 5,931,841 A | 8/1999 | Ralph |
| 5,976,145 A | 11/1999 | Kennefick, III |
| 5,993,455 A | 11/1999 | Noble |
| 6,106,528 A | 8/2000 | Durham et al. |
| 6,117,138 A | 9/2000 | Burrows et al. |
| 6,120,504 A | 9/2000 | Brumback et al. |
| 6,129,764 A | 10/2000 | Servidio |
| 6,168,627 B1 * | 1/2001 | Huebner | 623/19.11 |
| 6,179,877 B1 | 1/2001 | Burke |
| 6,193,758 B1 | 2/2001 | Huebner |
| 6,193,759 B1 | 2/2001 | Ro et al. |
| 6,238,436 B1 | 5/2001 | Lob et al. |
| 6,264,699 B1 | 7/2001 | Noiles et al. |
| 6,299,648 B1 | 10/2001 | Doubler et al. |
| 6,306,174 B1 | 10/2001 | Gie et al. |
| 6,338,734 B1 | 1/2002 | Burke et al. |
| 6,355,068 B1 | 3/2002 | Doubler et al. |
| 6,383,225 B2 | 5/2002 | Masini |
| 6,440,171 B1 | 8/2002 | Doubler et al. |
| 6,613,092 B1 | 9/2003 | Kana et al. |
| 2002/0040244 A1 | 4/2002 | Despres, III et al. |
| 2002/0099447 A1 | 7/2002 | Mears et al. |
| 2002/0116067 A1 | 8/2002 | Mears et al. |
| 2002/0120343 A1 | 8/2002 | Doubler et al. |
| 2002/0128720 A1 | 9/2002 | Masini |
| 2003/0028198 A1 * | 2/2003 | Tornier et al. | 606/99 |
| 2003/0135211 A1 * | 7/2003 | Cho | 606/62 |
| 2003/0158606 A1 | 8/2003 | Coon et al. |
| 2003/0204268 A1 | 10/2003 | Gerbec et al. |
| 2003/0204269 A1 | 10/2003 | Gerbec et al. |
| 2003/0220698 A1 | 11/2003 | Mears et al. |

OTHER PUBLICATIONS

"Answer® Hip System Surgical Technique," brochure Biomet Orthopedics, Inc. Copyright 2001 (11 sheets).

"Impact Modular™ Total Hip System," brochure, Biomet, Inc., Copyright 1992.

"Mallory-Head Radial™ Acetabular Shell," brochure Biomet, Inc. Copyright 1998 (2 sheets).

"Osteocap RS™ Hip System Surgical Technique," brochure, Biomet Orthopedics, Inc. Copyright 2001 (12 sheets).

"Stanmore™ Modular Hip System," brochure, Biomet, Inc. Copyright 1998 (12 sheets).

"Taperloc® Hip System," brochure, Biomet, Inc. Copyright 2000 (13 sheets).

\* cited by examiner

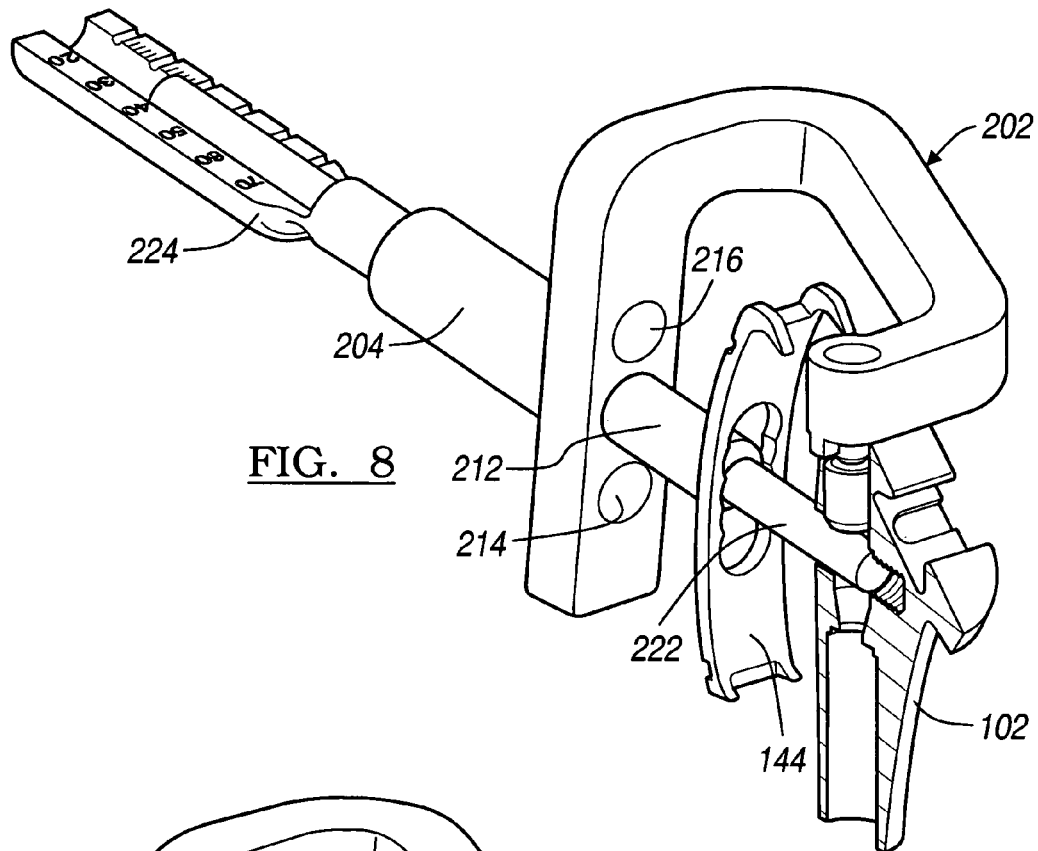
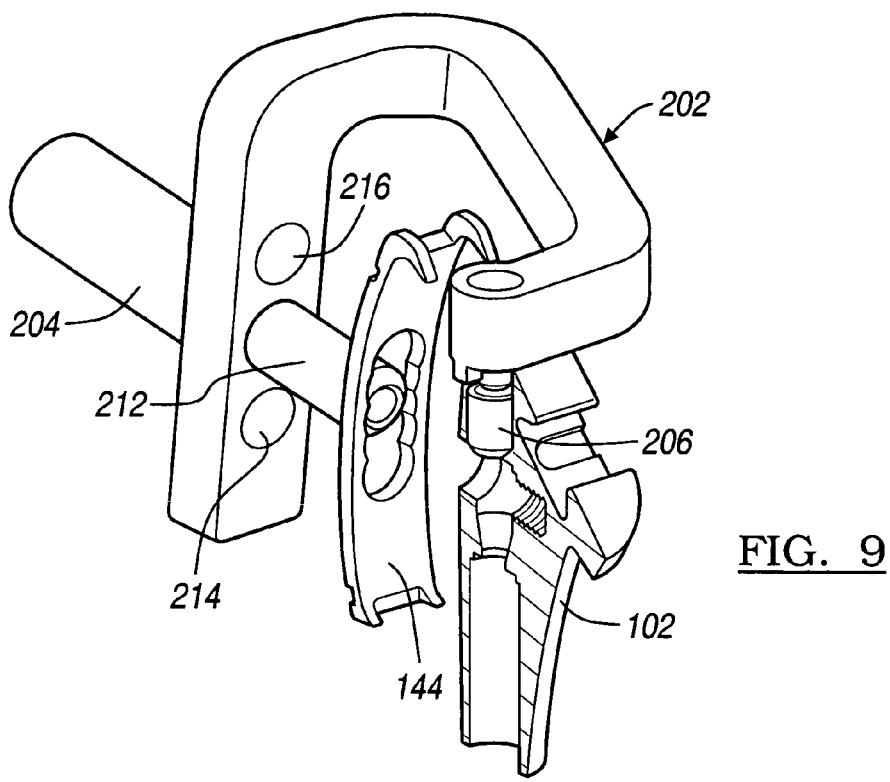

US 7,179,259 B1

INSTRUMENT ASSEMBLY FOR LATERAL IMPLANT

CROSS REFERENCE TO RELATED APPLICATIONS

This application is related to U.S. application Ser. No. 10/862,150 filed Jun. 4, 2004. The disclosure of the above application is incorporated herein by reference.

In many reconstructive procedures of the hip joint, the greater trochanter is sometimes resected from the proximal femur to provide access to the joint and/or a prosthetic implant. The resected portion is re-attached after a prosthetic femoral component is implanted, using, for example, trochanteric bolts, wires, nails, etc., with or without the use of support plates. The greater trochanter may also fracture unintentionally during the insertion of a prosthetic stem or during revision surgery, and may require re-attachment. The greater trochanter may also be supported and protected prophylactically as part of a primary or revision reconstructive procedure.

There is, therefore, a need for improved implants and associated instruments that facilitate lateral access to a stem prosthesis and allow easy insertion and removal of trochanteric bolts.

SUMMARY

The present teachings provide an instrument assembly for inserting a lateral fastener into a lateral blind bore of a stem body implanted into a bone. The instrument assembly includes an outrigger having an alignment tube extending laterally from the stem body, wherein the outrigger can be coupled with the stem body such that the alignment tube extends coaxially with the blind bore.

The present teachings provide an instrument assembly for attaching a fragment to a bone with a fastener. The instrument assembly includes an outrigger having an alignment tube and removably attachable to the bone, and a sleeve movably attachable to the alignment tube, wherein the sleeve is operable to compress and stabilize the fragment against the bone.

The present teachings also provide a modular hip implant kit that includes a modular hip implant assembly including at least one stem body, at least one lateral fastener, and an instrument assembly for fastening the lateral fastener into a bore of the stem body.

The present teachings also provide a method for repairing a bone. The method includes implanting a stem body having a lateral bore into a longitudinal canal of the bone, attaching an outrigger to the stem, positioning the outrigger to circumvent soft tissue adjacent to the bone, positioning an alignment tube of the outrigger substantially coaxially with the lateral bore of the stem body; drilling a lateral hole in the bone through the tube, and implanting a lateral fastener through the lateral hole of the bone into the lateral bore of the stem.

The present teaching provide a method for attaching fragment to a bone with a fastener. The method includes providing an outrigger having an alignment tube, attaching a sleeve to the tube, pressing the sleeve against fragment, stabilizing the fragment, removing the sleeve, and inserting the fastener through the alignment tube.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 4–13 are sequential perspective views of the instrument assembly of FIG. 1 illustrating the use of the instrument assembly of FIG. 1 in various stages of engagement.

DETAILED DESCRIPTION

The following description is merely exemplary in nature and is in no way intended to limit the invention, its application, or uses. In particular, the invention can be used with any type of prosthesis for a bone such as, for example, a proximal or distal femur, a proximal or distal tibia, a proximal or distal humerus, etc.

Figure 1:
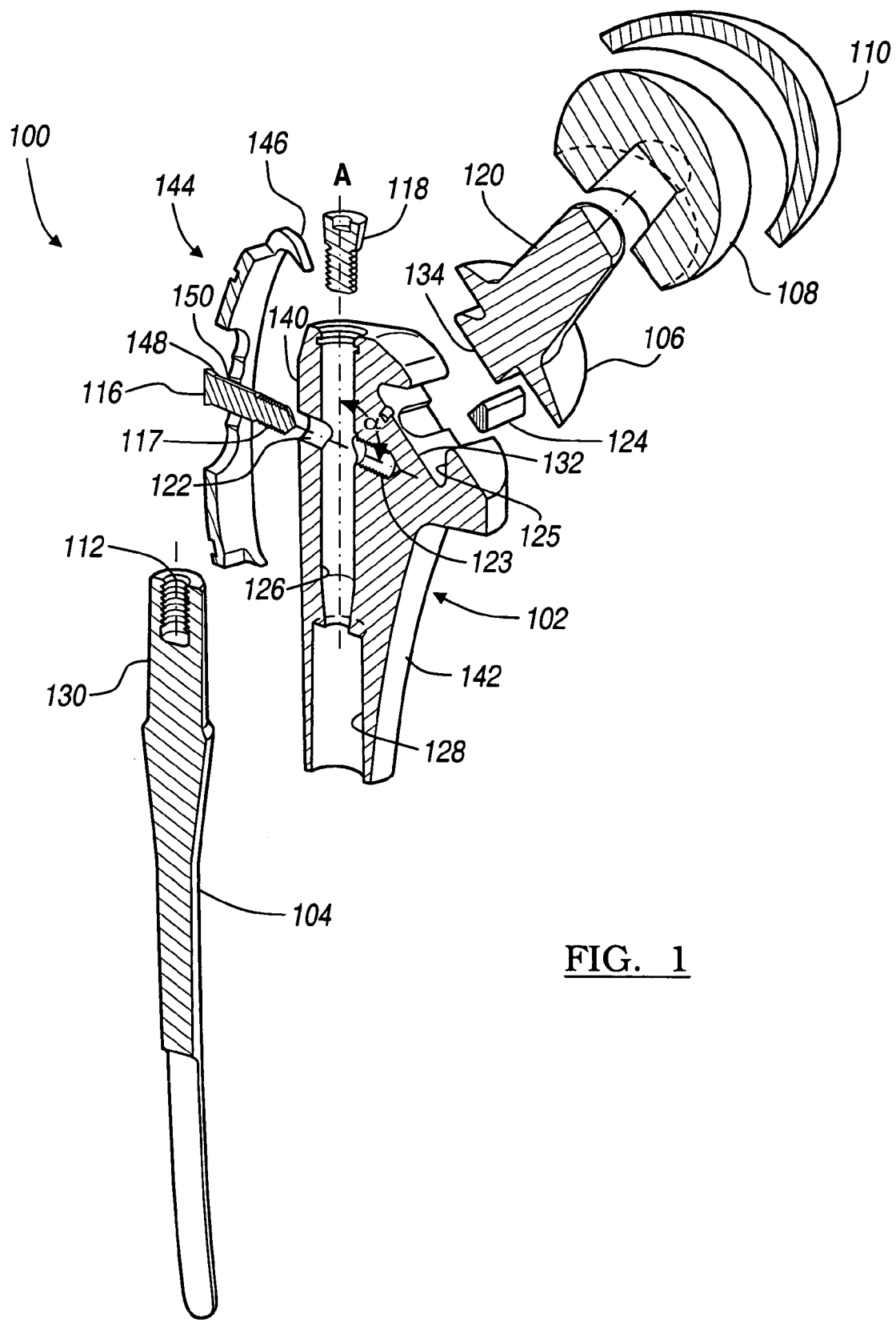
FIG. 1 is an exploded sectional view of an implant according to the present teachings.
Figure 2:
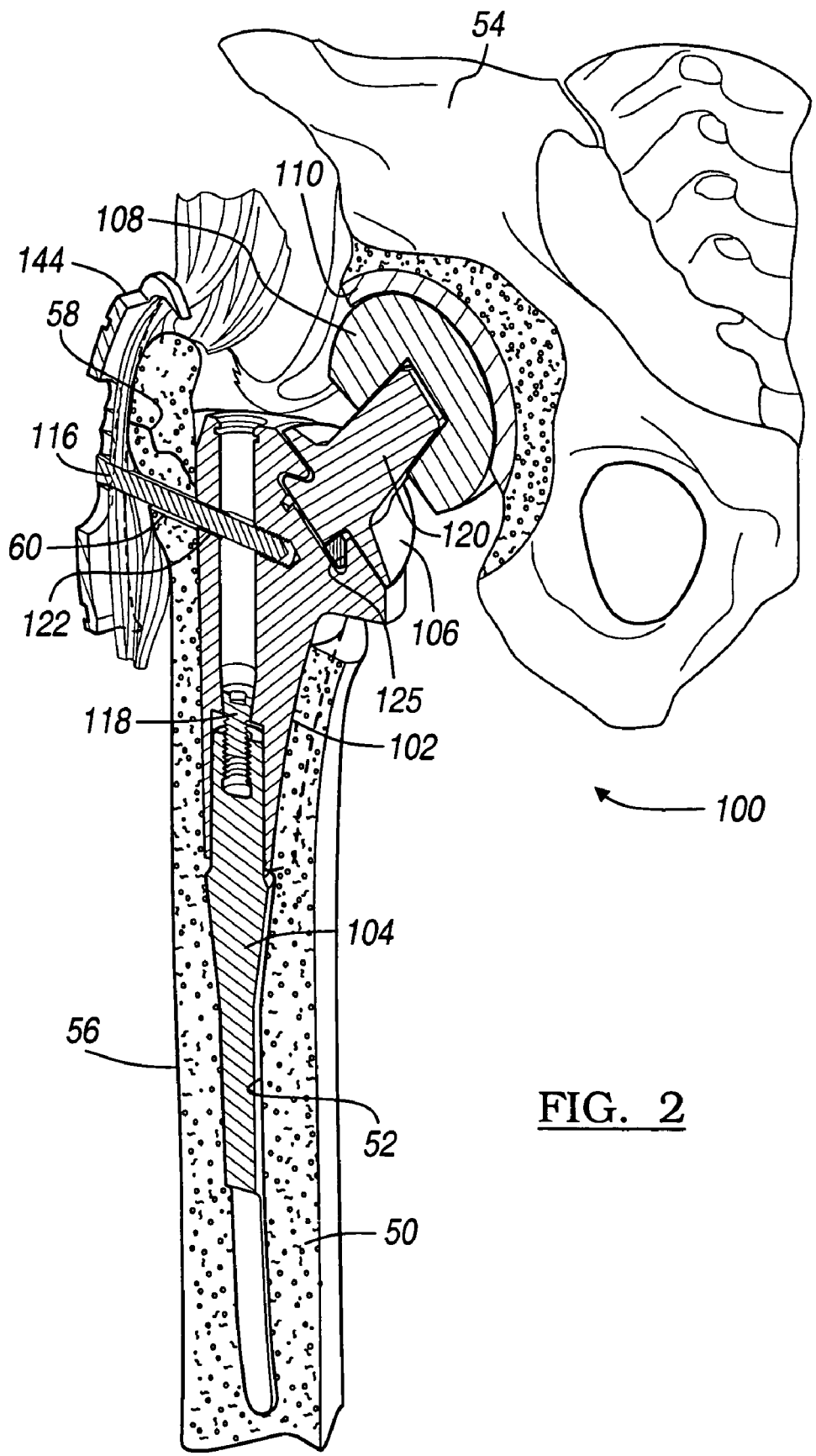
FIG. 2 is an exploded sectional environmental view of an implant according to the present teachings.

Referring to FIGS. 1 and 2, an exemplary implant 100 according to the present teachings includes a stem body 102 having a longitudinal axis A and a lateral blind bore 122 that extends from a lateral side 140 toward a medial side 142 of the stem body 102 at an angle α, without actually surfacing on the medial side 142. The blind bore 122 has, therefore a proximal to distal angulation of $\beta=\alpha-90°$. The angle β can be, for example, about 7°, although particular values depend on each application, as is discussed below. It should be appreciated that although the implant 100 is illustrated as a hip joint implant, the invention is not so limited. Thus, the implant 100 could be any implant associated with a long bone 50 and in situations where lateral stabilization, lateral access for revision, and lateral fracture repair or prevention are desirable.

The implant 100 further includes a lateral fastener 116 having a head 148. The lateral fastener 116 can be, for example, a trochanteric bolt when the long bone 50 is a proximal femur. The lateral fastener 116 is inserted into the lateral blind bore 122 from the lateral side 56 of the bone through a lateral hole 60 drilled into the bone 50. The lateral hole 60 is coaxial with the lateral blind bore 122 of the stem body 102 and can be drilled using the instrument assembly 200 of FIG. 4, as discussed below. The lateral fastener 116 can have a threaded portion 117 engaging a threaded portion 123 of the lateral blind bore 122.

The implant 100 may also include a lateral support or claw plate 144, which is implanted laterally in soft tissue adjacent to the lateral side 56 of the long bone 50 to reinforce the lateral side 56 of the bone 50 or provide support for a bone fragment 58, such as portion of a trochanter, broken off or resected from the lateral side 56 of the bone 50. The lateral support plate 144 is retained in position by the head 148 of the lateral fastener 116, with the head 148 received in a countersunk bore 150 of the support plate 144. The support plate 144 can have a variety of shapes depending on the particular application and can also be anatomically configured, having a shape that conforms to the shape of the lateral side 56 of the bone 50 or the bone fragment 58. The support plate 144 can also include anchors 146 for soft tissue attachment.

As illustrated in FIG. 2, the stem body 102 can be at least partially received in a longitudinal canal 52 of the long bone 50, such as, for example, the intramedullary canal of a femur. The stem body 102 can be an integral femoral component or a part of a modular femoral component that includes a stem extension 104. The stem extension 104 can be coupled to the stem body 102 with a Morse taper connection, such that a proximal tapered end 130 of the stem extension 104 is press-fitted into a distal tapered bore 128 of the stem body 102. The stem extension 104 and the stem body 102 can be locked with a longitudinal threaded fastener 118 that is received into a longitudinal bore 126 of the stem body 102 and engages a threaded bore 112 of the stem extension 104.

Other modular components of the implant 100 can include a neck component 106, a femoral head 108 and an acetabular cup 110, but some of these components may also be integrally combined. The neck component 106, for example, can be integral with the head 108, or alternatively, modularly coupled to the head 108 via a Morse taper connection. Or the neck component 106 can be integral with the stem body 102 or modularly coupled to the stem body with a Morse taper connection or with a dovetail/semi-dovetail connection, as illustrated in FIGS. 1 and 2 and described in co-pending, co-owned U.S. patent application Ser. No. 10/862,150 filed on Jun. 4, 2004, and entitled Modular Hip Joint Implant, the entire contents of which are incorporated by reference herein. Briefly, in the dovetail/semi-dovetail connection, the stem body 102 includes a dovetail slot 132 which receives a semi-dovetail projection 136. A key 124 is inserted a keyway 125 defined between the dovetail slot 132 and the semi-dovetail projection 136, for locking the stem body 102 to the neck component 106.

Figure 3:
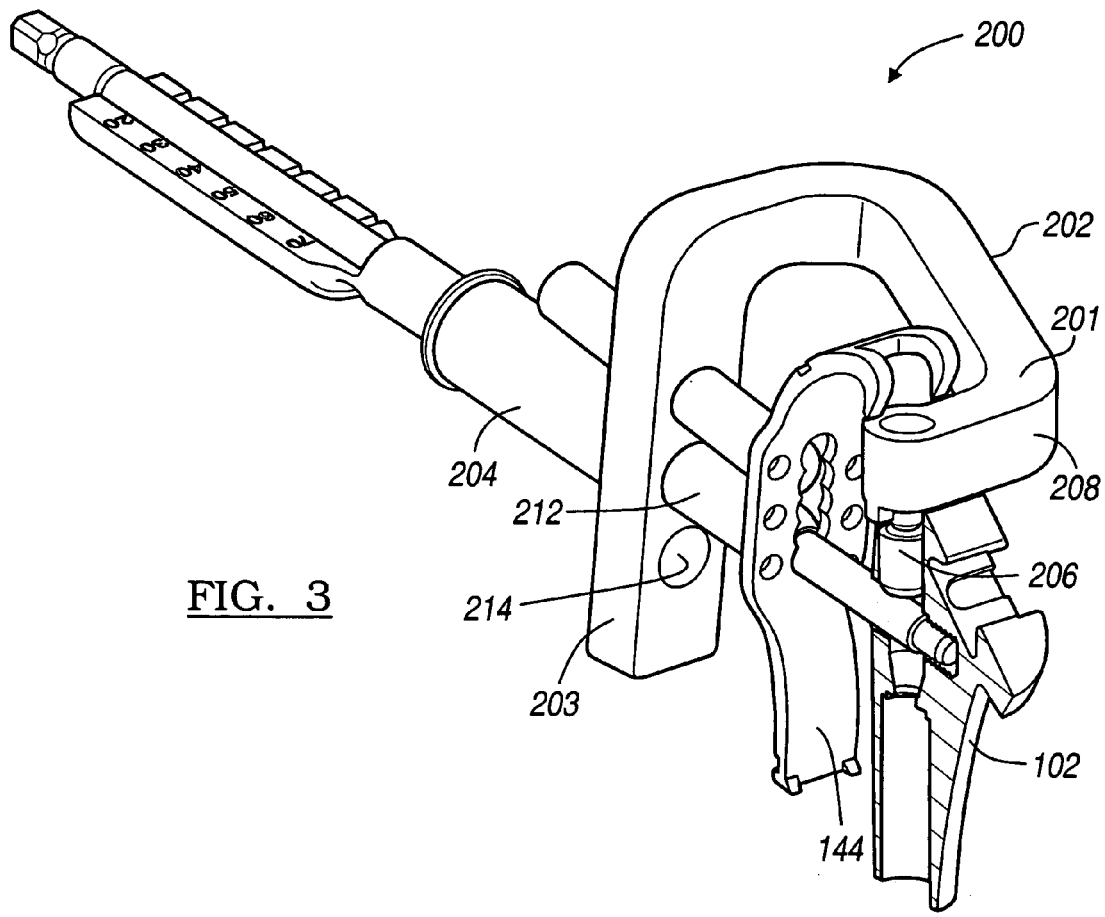
FIG. 3 is a perspective view of an instrument assembly with a left-handed outrigger coupled to an associated implant according to the present teachings.
Figure 3A:
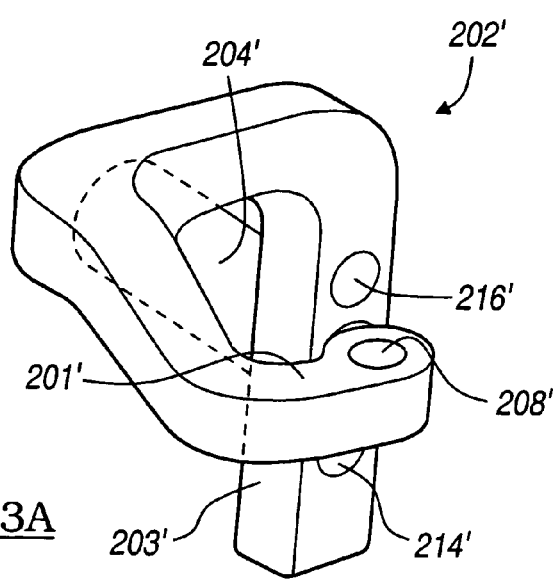
FIG. 3A is a perspective view of a right-handed outrigger according to the present teachings.

The stem body 102 can be implanted using a minimally invasive technique through a small anterior or posterior incision on the left or right femur. Referring to FIGS. 3 and 3A, after the stem body 102 is implanted, the lateral fastener 116 and the lateral support plate 144, if used, can be implanted using an instrument assembly 200. In the exemplary application in which the modular implant 100 includes a dovetail to semi-dovetail connection between the stem body 102 and the neck component 106, the instrument assembly 200 allows the lateral fastener 116 to be inserted after the implant 100 is implanted and fully assembled. The instrument assembly 200 includes an outrigger 202, 202' that can be coupled with the stem body 102. The outrigger 202, 202' is sized to be substantially rigid, avoiding misalignments caused by flexing. The outrigger 202, 202' has a "handedness" and is configured to avoid the abductor muscles 53 of the hip joint during the implantation of the lateral fastener 116. The "left-handed" outrigger 202 illustrated in FIG. 3 can be used laterally with anterior incisions of the left femur or posterior incisions of the right femur. The "right-handed" outrigger 202' illustrated in FIG. 3A is a mirror-image of the left-handed outrigger 202, and can be used laterally with anterior incisions of the right femur or posterior incisions of the left femur. The same numerals, unprimed and primed, respectively, are used to refer to corresponding elements of the left-handed and right-handed outriggers 202, 202'.

Each outrigger 202, 202' includes a C-shaped arm 201, 201' for circumventing the abductor muscles 53, and a leg 203, 203' extending from the arm 201, 201'. In use, the leg 203, 203' is positioned laterally and substantially parallel to the longitudinal axis A. An alignment tube 204, 204' extends laterally from an opening 210, 210' of the leg 203, 203'. The alignment tube 204, 204' can be integrally or modularly coupled with the leg 203, 203'. In the following, reference is primarily made to the left-handed outrigger 202 with the understanding that similar considerations are applicable to the right-handed outrigger 202'.

With continued reference to FIG. 3, the outrigger 202 is coupled to the stem body 102 with a dowel or other coupler/coupling mechanism 206 that is inserted through a hole 208 at the free end of the arm 201 into the longitudinal bore 126 of the stem body 102. Various other couplers 206 can be used, such as, for example, threaded fasteners or bolts, with or without springs, O-rings/seals or spring clips, clamps, etc. The coupler 206 is configured and sized to help locate the lateral blind bore 122 along the longitudinal bore 126. Thus, when the outrigger 202 is coupled to the stem body 102, the alignment tube 204 is coaxial with the lateral blind bore 122.

Referring to FIGS. 3, 4–13, the instrument assembly 200 can include a removable sleeve 212, which can be coaxially coupled to the alignment tube 204, for example, by threading, to extend medially from the leg 203. The alignment tube 204 and the sleeve 212 can support and align a drill 220 for drilling the lateral hole 60 into the bone 50 coaxially with the blind bore 122, and can also support and align a depth rod 222 with a scale 224 attached thereon for sizing the length of the lateral fastener 116 that needs to be used in the particular procedure. The drill 220 can be cannulated. The sleeve 212 can be used to compress the support plate 144 against soft tissue before the lateral fastener 116 is implanted. The leg 203 of the outrigger 202 can include first and second holes 214, 216 for receiving first and second retainer rods 226 on each side of the alignment tube 204 to retain the support plate 144 for inserting the lateral fastener 116 after the sleeve 212 is removed, as described below. Similarly, the support plate 144 can include in addition to the countersunk bore 150 for receiving the bolt 116 (or sleeve 212 or depth rod 222 or drill 220), a pair of countersunk retainer opening on each side of the bore 150 for coupling to tapered or shouldered ends 227 of the retainer rods 226. Alternatively, the support plate 144 can have an elongated opening 145 that replaces both the bore 150 and the pair of retainer openings, and includes instead suitably countersunk couplers instead of separate openings to hold the retainer rods 226.

Figure 4:
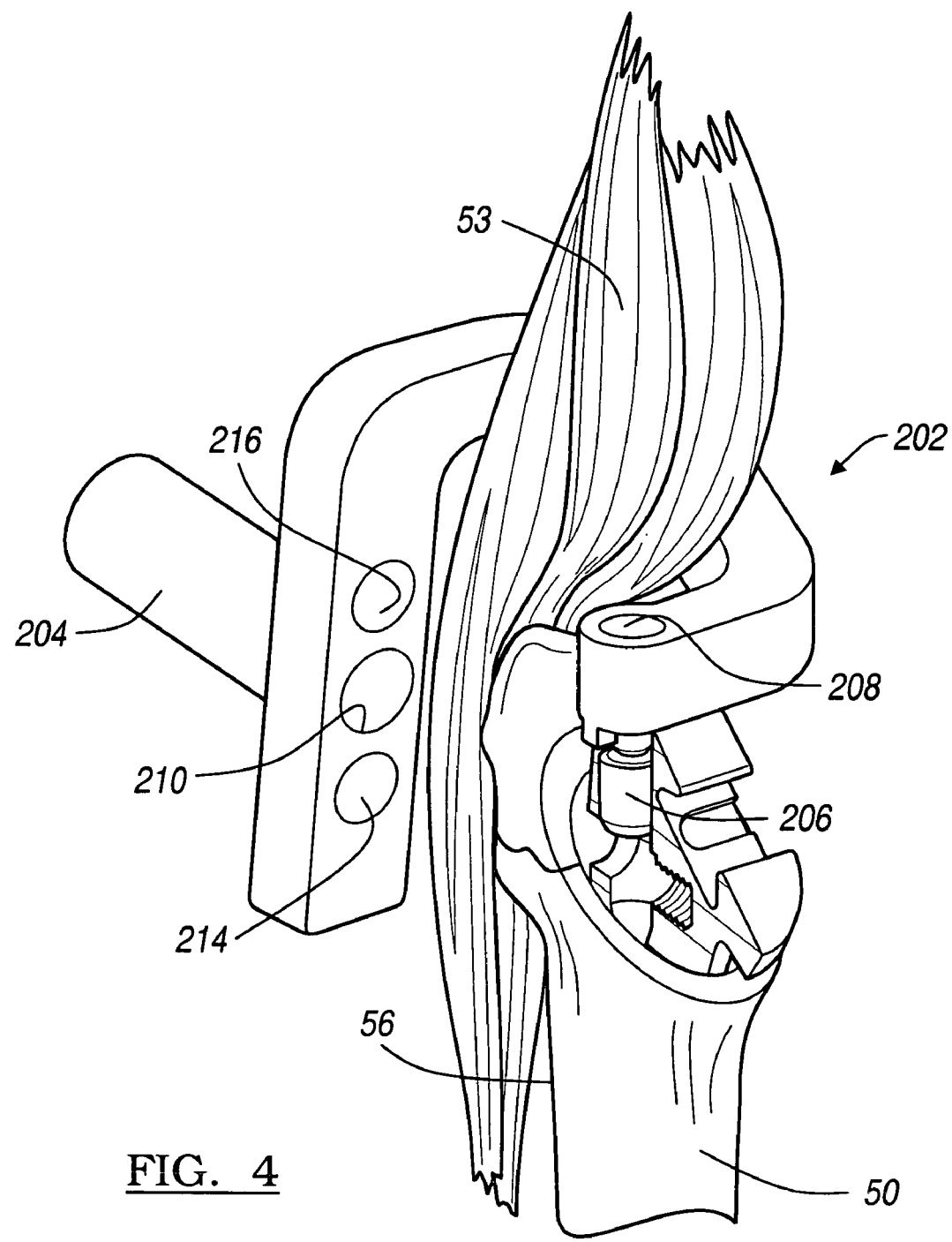
Figure 5:
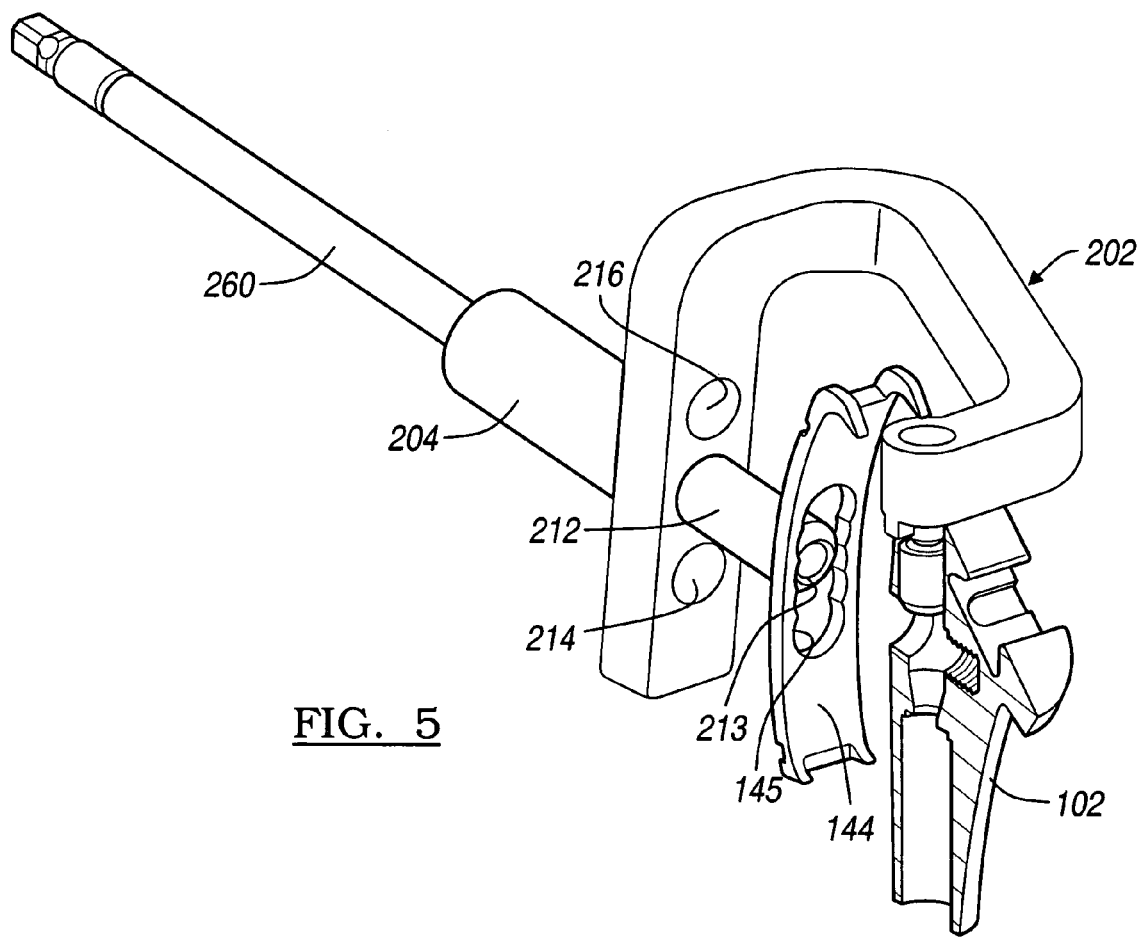
Figure 6:
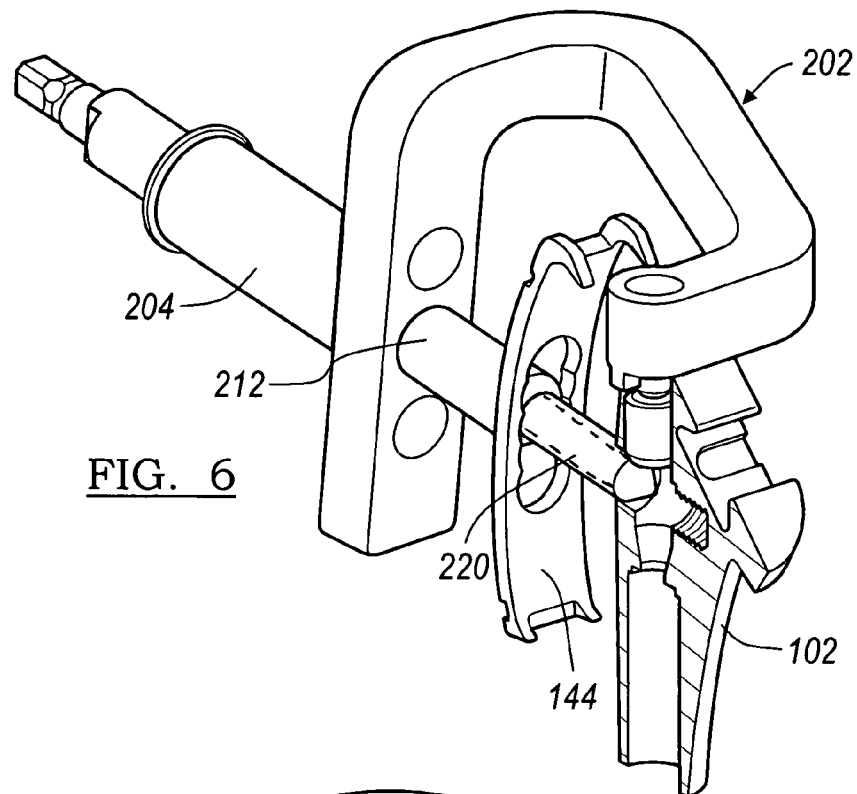
Figure 7:
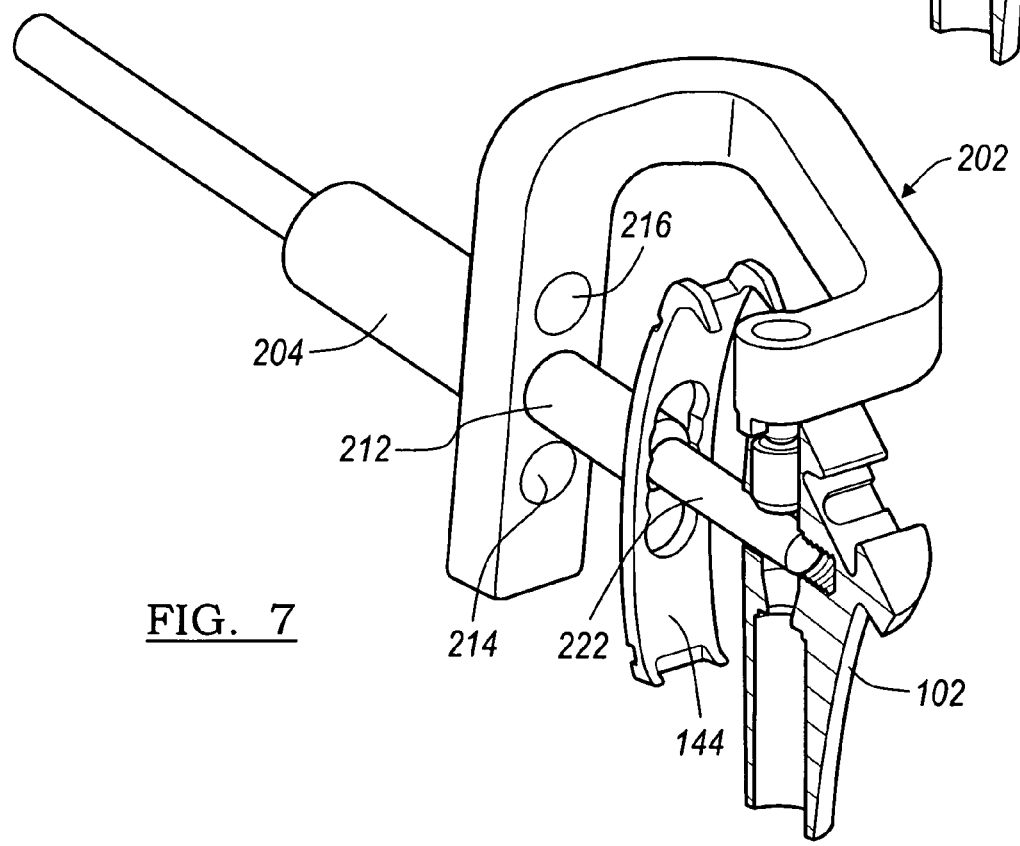

Referring to FIGS. 4–13, a procedure for inserting the lateral fastener 116 and the support plate 144 is outlined. Although the procedure is illustrated with the left-handed outrigger 202, the right-handed outrigger could be selected for use in the same sequence, for an appropriate incision-femur combination, as discussed above. The outrigger 202 is first coupled to the stem body 102 using the coupler 206, such that the alignment tube 204 is aligned coaxially with the blind bore 122, as shown in FIG. 4. Referring to FIG. 5, the support plate 144, if used, is implanted and compressed against soft tissue adjacent to the lateral side 56 of the bone 50 using a first end 213 of the sleeve 212, which is suitably configured for this purpose. A driver 260 can be coupled to the sleeve 212 to help compress the support plate 144. Referring to FIGS. 6 and 2, the drill 220 is inserted through the sleeve 212 to drill the lateral hole 60 into the bone 50 from the lateral side 56. Referring to FIGS. 7 and 8, after the drill 220 is removed, the depth rod 222 is inserted, and the scale 224 is coupled to the depth rod 222 to measure the required length of the lateral fastener 116. Because measurement occurs while the outrigger 202 is fully clamped and the support plate 144 is compressed against soft tissue, the required length of the lateral fastener 116 can be determined accurately. Referring to FIG. 9, the scale 224 and the depth rod 222 are removed, while the support plate 144 is still held compressed in place by the sleeve 212.

Figure 10:
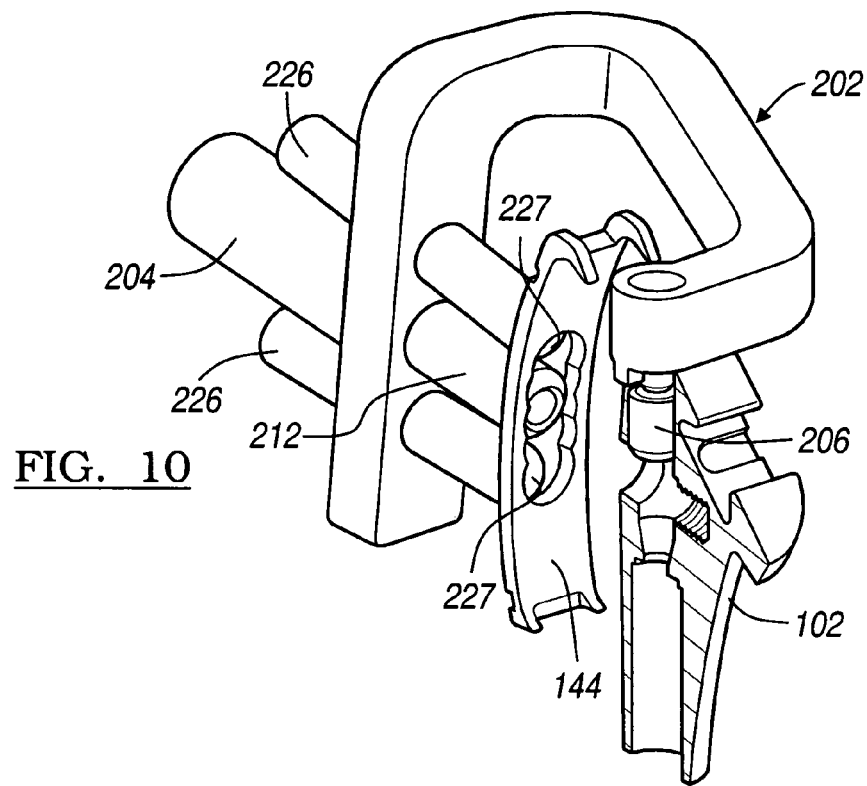
Figure 11:
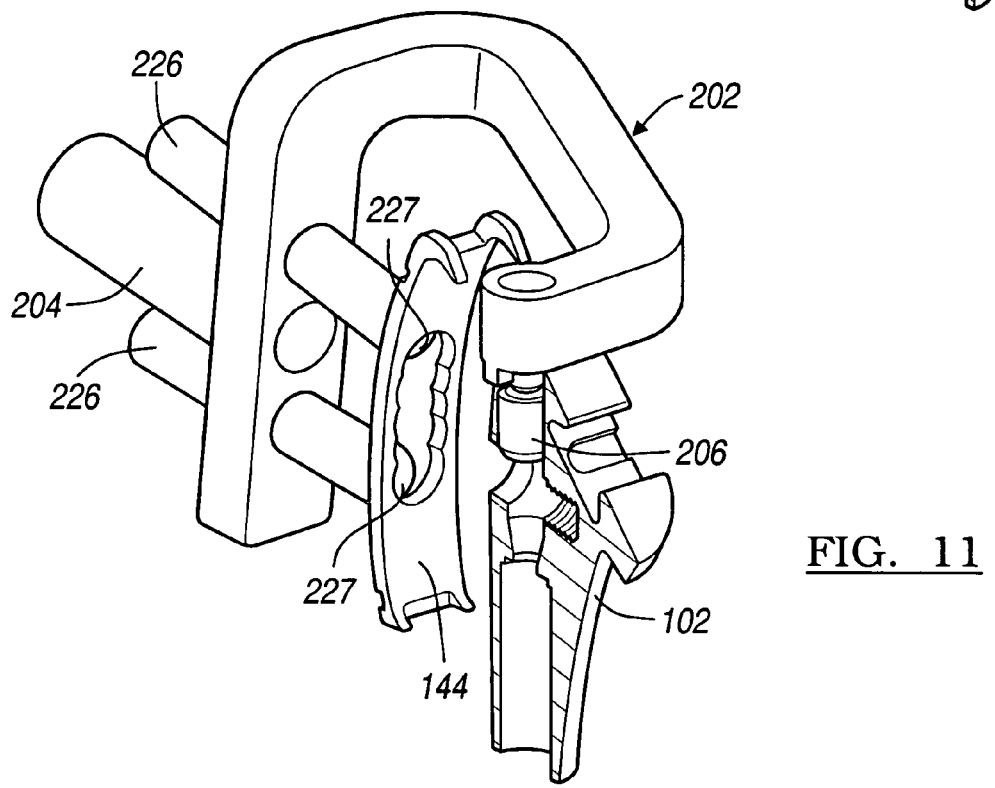
Figure 12:
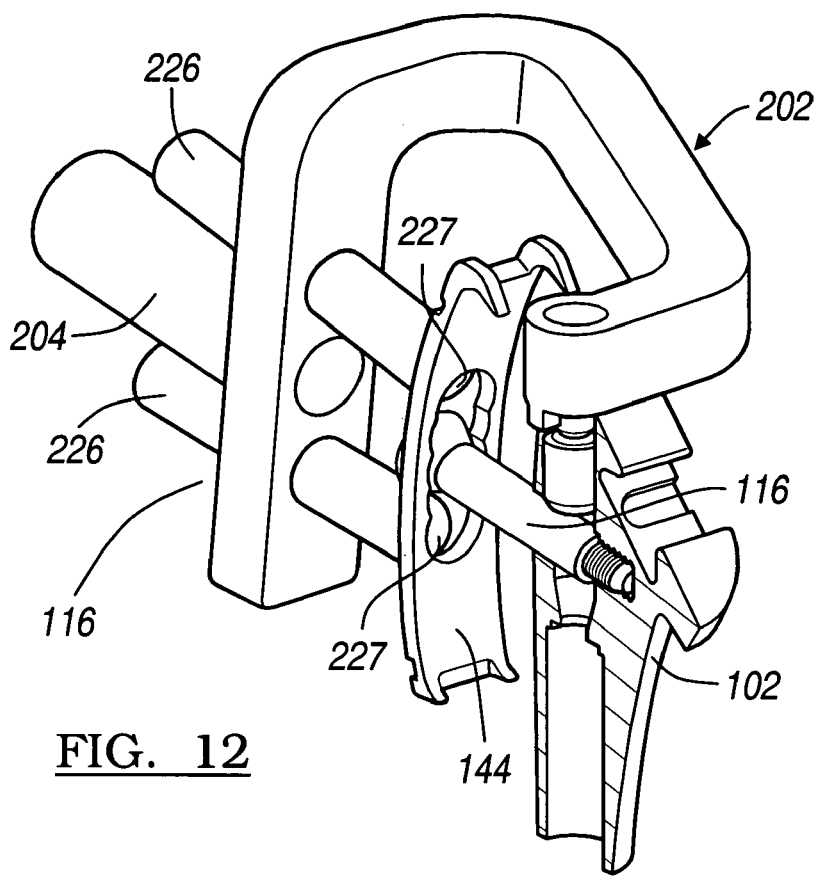
Figure 13:
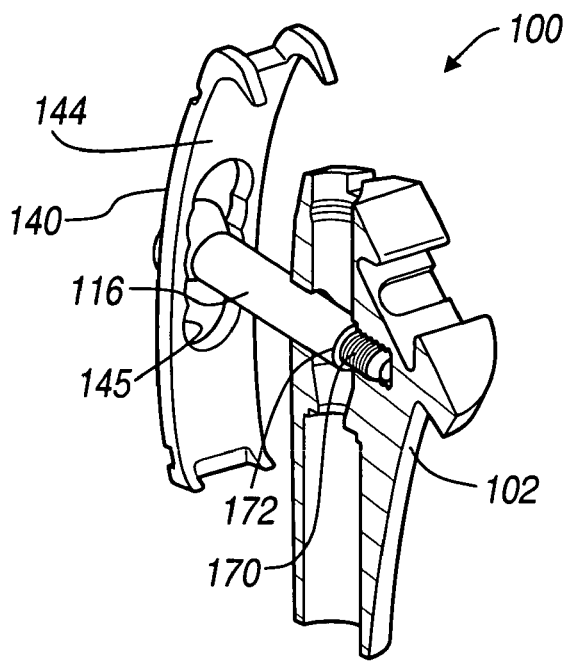

Referring to FIGS. 10 and 11, the retainer rods 226 are first positioned to stabilize and retain the support plate 144 in place, and then the sleeve 212 is removed. Referring to FIGS. 12 and 2, the lateral fastener 116 is inserted through the lateral bore 60 of the bone 50 and coupled to the lateral blind bore 122 of the stem body 102. The lateral fastener 116 can be configured to eliminate loosening and backing out by including, for example, a spiral lock thread 170, a shoulder 172, or other end loading feature. As the lateral fastener 116 is tightened along the inclined blind bore 122 of the stem body 102, the head 148 of the lateral fastener 116 pulls the support plate 144 and the bone fragment 58, if any, downward by an amount that depends on the value of the angle α and other sizing parameters. Referring to FIG. 13, the outrigger 202 and the retainer rods 226 are removed, completing the procedure.

By selectively using left-handed or right-handed outriggers 202, 202', the surgeon can insert the lateral fastener 116 laterally into a left or right long bone 50 while controlling the location of the incision, anteriorly or posteriorly. The lateral fastener 116 can be removed at a later procedure from the lateral side, leaving the empty blind bore 122 without access to joint space, and thereby reducing the severity of the surgical procedure and eliminating one source of possible contamination and infection of the joint.

The stem body 102 can be made of a titanium alloy or other biocompatible metal with or without plasma coating. The lateral fastener 116 and the support plate 144 can be made of a cobalt alloy or other biocompatible metal. The outrigger 202 and the retainer rods 226 can be made of stainless steel.

While in the foregoing the instrument assembly 200 was described for use with a lateral procedure, the invention is not so limited. Referring to FIGS. 3 and 3A, each of the right-handed 202, left-handed 202' outriggers can also be used with medial procedures to stabilize and provide support for a medially implanted fastener, such as bolt or nail, to compress the associated tissues and stabilize a bone fragment and/or a support plate for the bone fragment, as described above in connection with lateral procedures.

Figure 3B:
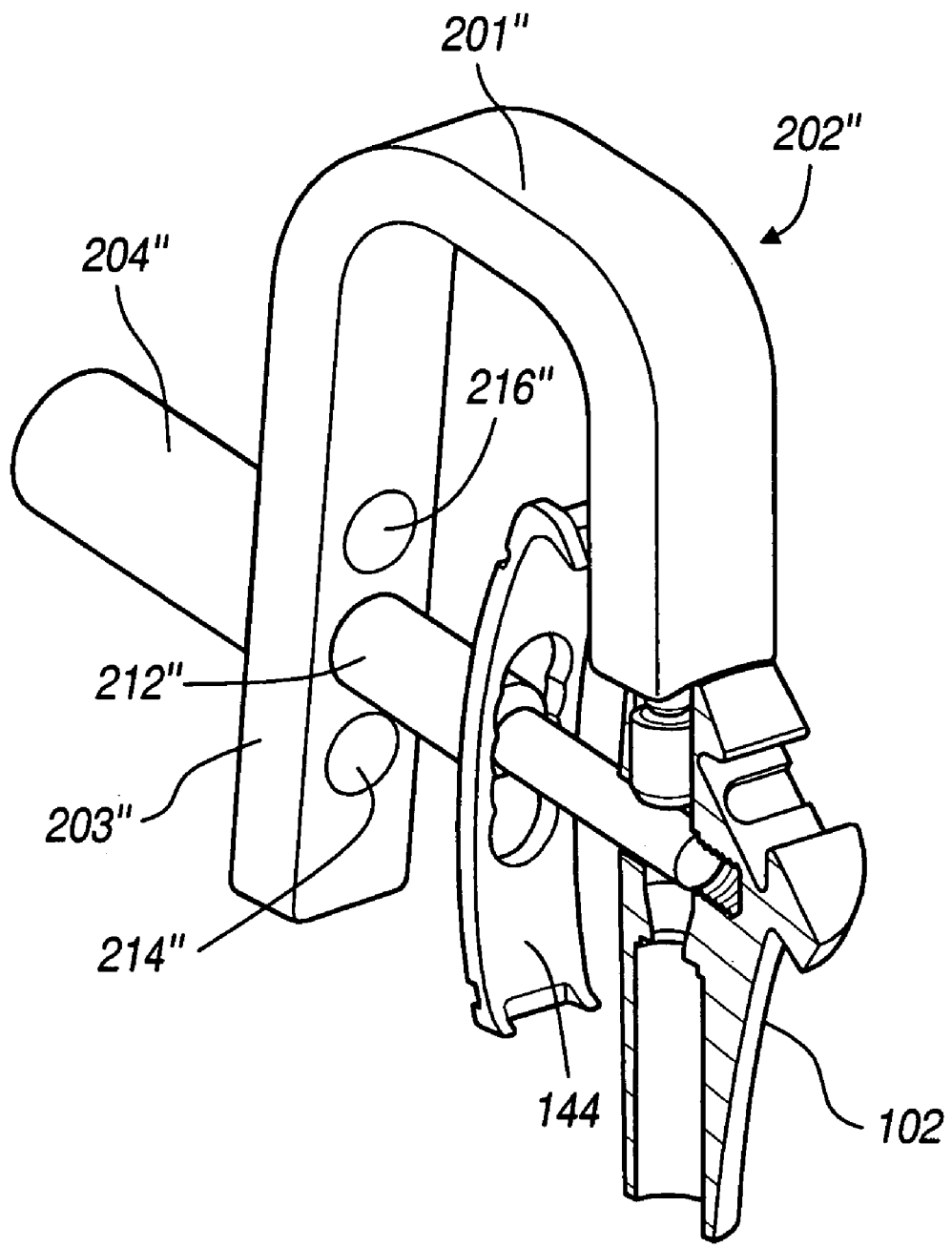
FIG. 3B is a perspective view of an instrument assembly with an even-handed outrigger according to the present teachings.

Referring to FIG. 3B, an even-handed outrigger 202" can be used medially or laterally with the instrument assembly 200. The even-handed outrigger 202", includes a leg 203" and an arm 201" which are substantially co-planar, such that when the outrigger 202" is used for a hip joint procedure, the arm 201" can pierce through, rather than circumvent, the abductor muscles. The even-handed outrigger 202" can include an alignment tube 204", a sleeve 212", holes 214", 216" for retainer rods, etc., as described in connection with the left and right handed outriggers 202, 202'.

While particular embodiments have been described in the specification and illustrated in the drawings, it will be understood by those skilled in the art that various changes may be made and equivalents may be substituted for elements thereof without departing from the scope of the invention as defined in the claims. In addition, many modifications may be made to adapt a particular situation or material to the present teachings without departing from the essential scope thereof. Therefore, it is intended that the present teachings are not to be limited to the particular embodiments illustrated by the drawings and described in the specification, but that the present teachings will include any embodiments falling within the foregoing description and the appended claims.

What is claimed is:

1. An assembly comprising:
   a modular hip implant assembly for a hip joint including at least one stem body implantable into a femoral bone, the stem body having a longitudinal axis and a lateral bore at an angle to the longitudinal axis at a proximal end of the stem body;
   at least one lateral fastener for insertion into the lateral bore;
   an implantable support plate configured for attachment to a lateral surface of the femur with the at least one lateral fastener;
   an instrument assembly for fastening the lateral fastener into the lateral bore of the stem body, the instrument assembly comprising:
   an outrigger including a leg and a C-shaped arm defining a plane at an angle relative to the leg, the C-shaped arm having first, second and third portions, the first portion extending at an angle from a proximal end of the leg, the second portion extending between the first and third portions, the first portion substantially parallel to the third portion, the third portion couplable to the a proximal end of the stem body, such that the lea is substantially parallel to the longitudinal axis of the stem body, and the first, second and third portions define a lateral opening that is substantially parallel to the longitudinal axis of the stem body and configured to allow the abductor muscles of the femoral bone to pass therethrough between the implantable support plate and the femoral bone; and
   an alignment tube extending from the leg such that the alignment tube is substantially coaxial with the lateral bore of the stem body.

2. The assembly of claim 1, wherein the outrigger is configured for selective use with an anterior incision on the left hip and a posterior incision on the right hip.

3. The assembly of claim 1, wherein the outrigger is configured for selective use with an anterior incision on the right hip and a posterior incision on the left hip.

4. The assembly of claim 1, further comprising a sleeve extending coaxially from the alignment tube between the leg and the support plate, the sleeve oriented transversely to the support plate, wherein the sleeve is configured to compress the support plate against soft tissue adjacent to a lateral side of the femur of the hip joint.

5. The assembly of claim 4, further comprising a removable depth rod receivable in the sleeve for sizing the lateral fastener.

6. The assembly of claim 5, further comprising a scale couplable to the depth rod.

7. The assembly of claim 6, further comprising at least one removable retainer rod for holding the support plate.

8. The assembly of claim 7, further comprising a cannulated drill.

9. The assembly of claim 1, wherein the first and second portions are perpendicular to the leg.

10. The assembly of claim 1, wherein the plane defined by the C-shaped arm is perpendicular to the leg.

11. The assembly of claim 1, wherein the support plate includes soft tissue fixation anchors.

12. The assembly of claim 1, wherein the support plate includes an opening for receiving the lateral fastener therethrough.

13. An assembly comprising:
    a modular hip implant assembly for a hip joint including at least one stem body implantable into a femoral bone, the stem body having a longitudinal axis and a lateral bore at an angle to the longitudinal axis at a proximal end of the stem body;
    at least one lateral fastener for insertion into the lateral bore;
    an implantable support plate configured for attachment to a lateral surface of the femur with the at least one lateral fastener;
    an instrument assembly for fastening the lateral fastener into the lateral bore of the stem body, the instrument assembly comprising:
        an outrigger including a leg and a C-shaped arm defining a plane at an angle relative to the leg, the C-shaped arm having first, second and third portions, the first portion extending from a proximal end of the leg substantially perpendicular to the leg, the second portion extending between the first and third portions and at an angle relative to the first portion, the third portion couplable to the a proximal end of the stem body, such that the leg is substantially parallel to the longitudinal axis of the stem body and the third portion is substantially perpendicular to the leg, and the first, second and third portions define a lateral opening that is substantially parallel to the longitudinal axis of the stem body and configured to allow the abductor muscles of the femoral bone to pass therethrough between the implantable support plate and the femoral bone; and
        an alignment tube extending from the leg, such that the alignment tube is substantially coaxial with the lateral bore of the stem body.

14. The assembly of claim 13, wherein the support plate includes an opening for receiving the lateral fastener therethrough.

15. An assembly comprising:
    a modular hip implant assembly for a hip joint including at least one stem body implantable into a femoral bone, the stem body having a longitudinal axis and a lateral bore at an angle to the longitudinal axis at a proximal end of the stem body;
    at least one lateral fastener insertable into the lateral bore of the stem body;
    an implantable support plate having an opening and configured for attachment to a lateral surface of the femur with the at least one lateral fastener, the at least one fastener passing through the opening, the implantable support plate including anchors for soft tissue attachment;
    an instrument assembly for fastening the lateral fastener into the lateral bore of the stem body, the instrument assembly comprising:
        an outrigger including a leg and a substantially planar arm at an angle relative to the leg, the planar arm having first, second and third portions defining a C-shape, the first portion extending from a proximal end of the leg substantially perpendicular to the leg, the second portion extending between the first and third portions and at an angle relative to the first portion, the third portion substantially perpendicular to the leg and couplable to the a proximal end of the stem body, such that the leg is substantially parallel to the longitudinal axis of the stem body, and the first, second and third portions define an opening that is substantially parallel to the longitudinal axis of the stem body and laterally spaced away from stem body, the opening configured to allow the abductor muscles of the femoral bone to pass therethrough between the implantable support plate and the femoral bone; and
        an alignment tube extending from the leg, such that the alignment tube is substantially coaxial with the lateral bore of the stem body.

16. The assembly kit of claim 15, wherein the alignment tube is an integral portion of the leg.

* * * * *

UNITED STATES PATENT AND TRADEMARK OFFICE
CERTIFICATE OF CORRECTION

PATENT NO.         : 7,179,259 B1                                            Page 1 of 1
APPLICATION NO.    : 10/862171
DATED              : February 20, 2007
INVENTOR(S)        : Philip M. Gibbs It is certified that error appears in the above-identified patent and that said Letters Patent is hereby corrected as shown below:

Column 1
Line 58, delete "teaching" and insert --teachings--.

Column 3
Line 37, insert --into-- after "inserted".

Column 6
Line 18 Claim 1, delete ":" and insert --;-- after fastener.
Line 28 Claim 1, delete "a" after "the" (3$^{rd}$ occurrence).
Line 29 Claim 1, delete "lea" and insert --leg--.

Column 7
Line 26 Claim 13, delete "a" after "the" (3$^{rd}$ occurrence).

Column 8
Line 26 Claim 15, delete "a" after "the" (2$^{nd}$ occurrence).

Signed and Sealed this

Sixth Day of January, 2009

JON W. DUDAS
*Director of the United States Patent and Trademark Office*